(12) United States Patent
Xu et al.

(10) Patent No.: US 7,270,814 B2
(45) Date of Patent: Sep. 18, 2007

(54) ODOR CONTROL COMPOSITIONS AND METHODS

(75) Inventors: Hui Xu, Wake Forest, NC (US); Henrik Lund, Vaerlose (DK); Jing Luo, Raleigh, NC (US); Kim Bloomfield, Raleigh, NC (US)

(73) Assignee: Novozyme A/S, Bagsvaerd (DK)

( * ) Notice: Subject to any disclaimer, the term of this patent is extended or adjusted under 35 U.S.C. 154(b) by 0 days.

(21) Appl. No.: 10/868,467

(22) Filed: Jun. 14, 2004

(65) Prior Publication Data

US 2005/0019315 A1    Jan. 27, 2005

Related U.S. Application Data

(60) Provisional application No. 60/478,464, filed on Jun. 14, 2003.

(51) Int. Cl.
*A61K 38/43* (2006.01)
*A61K 38/44* (2006.01)
*C12N 9/04* (2006.01)

(52) U.S. Cl. .................... 424/94.1; 424/94.4; 435/183; 435/189; 435/190

(58) Field of Classification Search ............... 424/94.1, 424/94.4; 435/183, 189, 190
See application file for complete search history.

(56) References Cited

U.S. PATENT DOCUMENTS

| 5,607,681 A | 3/1997 | Galley et al. |
| 5,804,170 A | 9/1998 | Negoshi et al. |
| 5,879,928 A * | 3/1999 | Dale et al. ................... 435/264 |
| 6,025,186 A | 2/2000 | Kirk et al. |
| 6,074,631 A | 6/2000 | Tsuchiya et al. |
| 6,080,391 A * | 6/2000 | Tsuchiya et al. .............. 424/65 |
| 6,165,761 A | 12/2000 | Schneider et al. |

FOREIGN PATENT DOCUMENTS

WO    0110195    2/2001

* cited by examiner

*Primary Examiner*—Ruth A Davis
(74) *Attorney, Agent, or Firm*—Jason I. Garbell

(57) ABSTRACT

The present invention relates to the use of a carbohydrate oxidase to reduce or prevent malodor. The present invention also relates to a deodorizing composition comprising a carbohydrate oxidase.

12 Claims, 2 Drawing Sheets

ODOR CONTROL COMPOSITIONS AND METHODS

FIELD OF THE INVENTION

The present invention relates to compositions and methods for controlling odors, e.g., odors emitted from industrial processes.

BACKGROUND OF THE INVENTION

A significant complaint about many industrial processes relates to the odors emitted from factories. Pulp and paper mills, for example, are notorious for producing objectionable odors (malodors), and such facilities often receive complaints from the surrounding community related to such odor emissions. Odor emissions are also often associated by the public with other serious environmental and health problems, e.g., carcinogen emissions and allergen production, even though the odor emission is not linked to such problems.

There are many different types of odors and sources of such odors in the environment. Odors in industrial processes are often caused by reduced sulfides, nitrogen containing compounds, and other organic compounds, such as, volatile short chain fatty acids. The odors are also generated during different stages of the industrial process, and may be caused, e.g., by microbial contamination or by chemical and/or biological agents present in the industrial process.

A number of solutions have been proposed to control the odor problems in the environment, including, for example, the substitution of agents which cause malodor with agents which causes reduced odor or no odor and/or the use of compositions and equipment (e.g., vaporizers) that neutralizes the odor and/or odor source.

U.S. Pat. No. 5,804,170, for example, discloses a deodorant composition comprising a phenolic compound and an enzyme which can oxidize the phenolic compound. The phenolic compounds are stated to have a deodorizing effect when used in combination with oxidases, such as, polyphenol oxidases, monophenol oxidases, peroxidases, laccases, tyrosinases, and glucose oxidases.

U.S. Pat. No. 6,074,631 discloses malodor reducing composition and methods involving the use of oxidoreductases in combination with a mediator to reduce malodor.

U.S. Pat. No. 6,025,186 discloses the use of haloperoxidase in combination with a hydrogen peroxide source for reducing malodor emanating from soiled hygiene products.

SUMMARY OF THE INVENTION

The present invention relates to the use of a carbohydrate oxidase to reduce or prevent malodor. In a preferred embodiment, the present invention relates to the use of a carbohydrate oxidase to reduce or prevent malodor caused by the degradation of carbohydrate materials into volatile short chain fatty acids, such as, butyric acid, lactic acid, acetic acid and propionic acid. Although not limited to any one theory of operation, the carbohydrate oxidase treatment is believed to reduce or prevent malodor by converting carbohydrates materials (e.g., sugars and other oligomers from carbohydrate materials) into organic acids, such as, gluconic acid, lactobionic acid, and/or cellobionic acid, so as to prevent or reduce the formation of volatile short chain fatty acids.

The present invention also relates to a deodorizing composition comprising a carbohydrate oxidase.

DETAILED DESCRIPTION OF THE INVENTION

Figure 1:
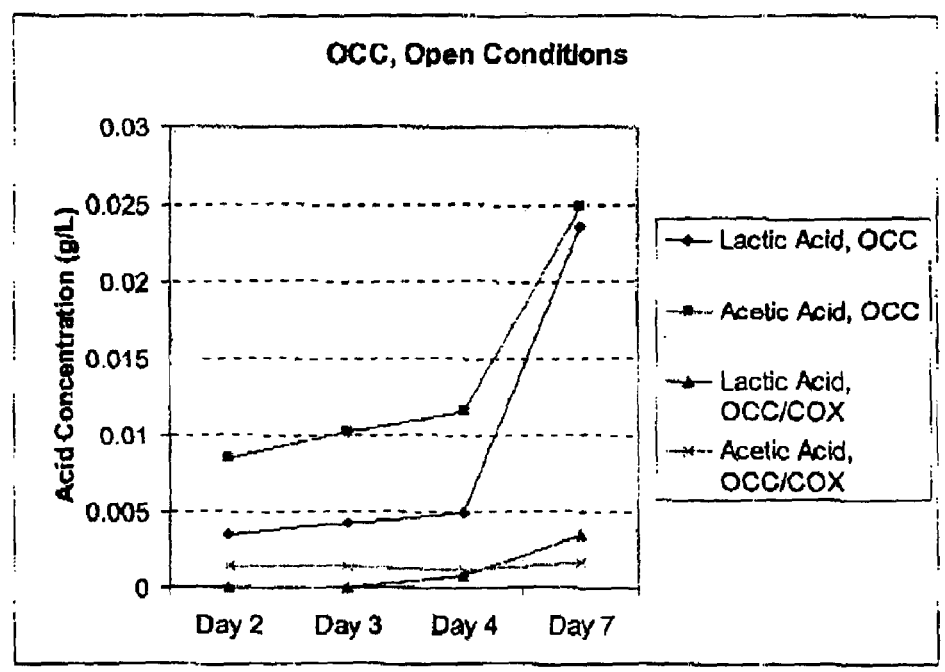
FIG. 1 is graph generated from HPLC data for lactic acid and acetic acid concentration (g/L) in OCC filtrate, under open atmospheric conditions.

A carbohydrate oxidase (EC 1.1.3) refers to an enzyme which is able to oxidize carbohydrate substrates. Preferably, the carbohydrate oxidase is able to inhibit the formation of short chain fatty acids (e.g., butyric acid, lactic acid, acetic acid and propionic acid) by converting a carbohydrate substrate (e.g., glucose or other sugar or oligomer intermediate) into an organic acid, e.g., gluconic acid, lactobionic acid, and/or cellobionic acid. Examples of carbohydrate oxidases include malate oxidase (EC 1.1.3.3), glucose oxidase (EC 1.1.3.4), hexose oxidase (EC 1.1.3.5), galactose oxidase (EC 1.1.3.9), pyranose oxidase (EC 1.1.3.10) catechol oxidase (EC 1.1.3.14), sorbose oxidase (EC 1.1.3.11) and cellobiose oxidase (EC 1.1.3.25), mannitol oxidase (EC 1.1.3.40). Preferred oxidases include monosaccharide oxidases, such as, glucose oxidase, hexose oxidase, galactose oxidase and pyranose oxidase.

The carbohydrate oxidase may be derived any suitable source, e.g., a microorganism, such as, a bacteria, a fungus or yeast. Examples of carbohydrate oxidases include the carbohydrate oxidases disclosed in WO 95/29996 (Novozymes A/S); WO 99/31990 (Novozymes A/S), WO 97/22257 (Novozymes A/S), WO 00/50606 (Novozymes Biotech), WO 96/40935 (Bioteknologisk Institute), U.S. Pat. No. 6,165,761 (Novozymes A/S), U.S. Pat. No. 5,879,921 (Novozymes A/S), U.S. Pat. No. 4,569,913 (Cetus Corp.), U.S. Pat. No. 4,636,464 (Kyowa Hakko Kogyo Co., Ltd), U.S. Pat. No. 6,498,026 (Hercules Inc.); and EP 321811 (Suomen Sokeri); and EP 833563 (Danisco A/S).

The glucose oxidase may be derived from a strain of *Aspergillus* or *Penicillium*, preferably, *A. niger, P. notatum, P. amagasakiense* or *P. vitale*. Preferably, the glucose oxidase is an *Aspergillus niger* glucose oxidase. Other glucose oxidases include the glucose oxidases described in "Methods in Enzymology", Biomass Part B Glucose Oxidase of *Phanerochaete chrysosporium*, R. L. Kelley and C. A. Reddy (1988), 161, pp. 306-317 and the glucose oxidase Hyderase 15 (Amano Pharmaceutical Co., Ltd.).

Hexose oxidase can be isolated, for example, from marine algal species naturally producing that enzyme. Such species are found in the family Gigartinaceae which belong to the order Gigartinales. Examples of hexose oxidase producing algal species belonging to Gigartinaceae are *Chondrus crispus* and *Iridophycus flaccidum*. Also algal species of the order Cryptomeniales are potential sources of hexose oxidase. Hexose oxidases have been isolated from several red algal species such as *Irido-phycus flaccidum* (Bean and Hassid, 1956, J. Biol. Chem., 218:425-436) and *Chondrus crispus* (Ikawa 1982, Methods Enzymol., 89:145-149). Additionally, the algal species *Euthora cristata* (Sullivan et al. 1973, Biochemica et Biophysica Acta, 309:11-22) has been shown to produce hexose oxidase. Other potential sources of hexose oxidase include microbial species or land-growing plant species. An example of a plant source for a hexose oxidase is the source disclosed in Bean et al., Journal of Biological Chemistry (1961) 236: 1235-1240, which is capable of oxidizing a broad range of sugars including D-glucose, D-galactose, cellobiose, lactose, maltose, D-2-deoxyglucose, D-mannose, D-glucosamine and D-xylose. Another example of an enzyme having hexose oxidase activity is the carbohydrate oxidase from *Malleomyces mallei* disclosed by Dowling et al., Journal of Bacteriology (1956) 72:555-580. Another example of a suitable hexose oxidase is the hexose oxidase described in EP 833563.

The pyranose oxidase may be derived, e.g., from a fungus, e.g., a filamentous fungus or a yeast, preferably, a Basidomycete fungus. The pyranose oxidase may be derived from genera belonging to Agaricales, such as *Oudemansiella* or *Mycena*, to Aphyllophorales, such as *Trametes*, e.g. *T. hirsuta, T. versicolor T. gibbosa, T. suaveolens, T. ochracea, T. pubescens*, or to *Phanerochaete, Lenzites* or *Peniophora*. Pyranose oxidases are of widespread occurrence, but in particular, in Basidiomycete fungi. Pyranose oxidases have also been characterized or isolated, e.g., from the following sources: *Peniophora gigantea* (Huwig et al., 1994, Journal of Biotechnology 32, 309-315; Huwig et el., 1992, Med. Fac. Landbouww, Univ. Gent, 57/4a, 1749-1753; Danneel et al., 1993, Eur. J. Biochem. 214, 795-802), genera belonging to the Aphyllophorales (Volc et al., 198S, Folia Microbiol. 30, 141-147), *Phanerochaete chrysosporium* (Volc et al., 1991, Arch. Mirobiol. 156, 297-301, Volc and Eriksson, 1988, Methods Enzymol 161B, 316-322), *Polyporus pinsitus* (Ruelius et al., 1968, Biochim. Biophys. Acta, 167, 493-500) and *Bierkandera adusta* and *Phebiopsis gigantea* (Huwig et al., 1992, op. cit.) Another example of a pyranose oxidase is the pyranose oxidase described in WO 97/22257, e.g. derived from *Trametes*, particularly *T. hirsuta*.

Galactose oxidase enzymes are well-known in the art. An example of a galactose oxidase is the galactose oxidases described in WO 00/50606.

Commercially available carbohydrate oxidases include GLUZYME™ (Novozymes A/S) and GRINDAMYL™ (Danisco A/S), Glucose Oxidase HP S100 and Glucose Oxidase HP S120 (Genzyme); Glucose Oxidase-SPDP (Biomeda); Glucose Oxidase, G7141, G 7016, G 6641, G 6125, G 2133, G 6766, G 6891, G 9010, and G 7779 (Sigma-aldrich); and Galactose Oxidase, G 7907 and G 7400 (Sigma-aldrich).

The carbohydrate oxidase selected for use in the composition or treatment process of the present invention preferably depends on the carbohydrate source present in the system, process or composition to be treated. Thus, in some preferred embodiments, a single type of carbohydrate oxidase may be preferred, e.g., a glucose oxidase, when a single carbohydrate source is involved. In other preferred embodiments, a combination of carbohydrate oxidases will be preferred, e.g., a glucose oxidase and a hexose oxidase. Preferably, the carbohydrate oxidase is derived from a fungus belonging to the genus *Microdochium*, preferably the fungus is *Microdochium nivale*, such as *Microdochium nivale* as deposited under the deposition no CBS 100236, as described in U.S. Pat. No. 6,165,761 (Novozymes A/S.), which is hereby incorporated by reference. The *Microdochium nivale* carbohydrate oxidase has activity on a broad range of carbohydrate substrates.

The carbohydrate oxidase sample is preferably catalase-free to prevent degradation of hydrogen peroxidase used in subsequent processing steps.

The carbohydrate oxidase treatment may be used to control (i.e., reduce or prevent) malodor in any desired environment, such as, in a factory (e.g., factory effluent), machine, process stream (e.g., white water in a mill), sludge treatment plant, waste water treatment plant, lagoon, storage facility, waste or disposal container, and waste or disposal facility. In a preferred embodiment, the carbohydrate oxidase treatment is applied to malodor in waste water. In a preferred embodiment, the carbohydrate oxidase is used to prevent malodor caused by carbohydrate degradation, e.g., starch degradation (generally through a sugar intermediate) into short chain volatile acids, e.g., butyric acid, lactic acid, acetic acid and propionic acid.

The carbohydrate oxidase treatment is preferably carried out by contacting the source of the malodor (i.e., malodorous source) with the carbohydrate oxidase. As used herein, an "odiferous composition" refers to a composition which contains a malodorous source. In preferred applications, the malodor arises from (and the carbohydrate oxidase treatment applies to) the conversion of the carbohydrate substrate (e.g., starch, cellulose and/or hemicellulose substrate) to sugar molecules, such as, glucose, which are then converted to volatile short chained fatty acids. The conversion process is often caused by the action of microorganisms, enzymes and/or chemicals. Accordingly, when malodor arises by such conversion process or a similar conversion process, the carbohydrate oxidase treatment is preferably applied prior to or during the process or processes in which the conversion to the volatile short chain fatty acids occurs.

Accordingly, in a preferred embodiment, the carbohydrate oxidase is added to a composition comprising a carbohydrate substrate and a malodor generating agent. The malodor generating agent may be a microorganism (e.g., a bacteria or a fungus), an enzyme or a chemical (e.g., an acid or alkaline hydrolysis) which converts a carbohydrate substrate to short chained volatile fatty acids. Generally, for the best results, the carbohydrate oxidase is added directly to the carbohydrate substrate, e.g., waste water containing the carbohydrate substrate. Further, the deodorizing effect of the carbohydrate oxidase treatment of the present invention is not dependent on the presence of phenolic compounds, which need not be present during such treatment or in the deodorizing composition.

In other preferred embodiments, the carbohydrate oxidase is added in combination (such as, for example, sequentially or simultaneously) with a carbohydrate-degrading enzyme (e.g., a starch-degrading enzymes, such as an alpha-amylase or glucoamylase and/or a cellulose or hemicellulose degrading enzyme, e.g., cellulase or hemicellulase) to convert the carbohydrate material to substrates suitable for the carbohydrate oxidase.

The carbohydrate oxidase is added in an amount effective to reduce odor or to prevent odor, more preferably, to reduce the formation of volatile short chain fatty acids. Examples of effective amounts of carbohydrate oxidase include 0.01 mg-1 g enzyme protein/L, preferably, 0.1 mg-500 mg enzyme protein/L, and more preferably, 0.5 mg-100 mg enzyme protein/L.

The temperature and pH for the carbohydrate oxidase treatment is not critical, provided that the temperature and pH is suitable for the enzymatic activity of the carbohydrate oxidase. Generally, the temperature and pH will depend on the system, composition or process which is being treated. Suitable temperature and pH conditions include 5° C. to 120° C. and pH 1 to 12, however, ambient temperatures and pH conditions are preferred.

The treatment time will vary depending on, among other things, the extent of the malodor problem (e.g., the amount of carbohydrate material present and/or malodor generating agent) and the type and amount of the carbohydrate oxidase employed. The carbohydrate oxidase may also be used in a preventive manner, such that, the treatment time is continuous or carried out a set point in the process.

In a preferred embodiment, the present invention relates to the use of carbohydrate oxidase to reduce or prevent malodor in a pulp and paper mill. In pulp and paper mills, malodor is often caused by the conversion of starch, cellulose and hemicellulose from the furnish (e.g., wood substrate, mixed office waste or old corrugated cardboard) to short chain fatty acids, such as, butyric acid, lactic acid, acetic acid and propionic acid. The conversion process may be due from a number of sources, e.g., from microorganisms, biological agents (e.g., enzymes) or chemicals present in pulp and paper processing. Malodor in pulp and paper mills, and other industrial processes, is becoming even more of a problem as such processes and facilities move to closed water system or loops (e.g., white water or waste water) which lead to a build up of starch and other carbohydrate sources. Although not limited, for pulp and paper processes, the temperature and pH will generally be 15° C. to 65° C., and pH 3 to 9.

In a preferred embodiment, malodor in a pulp and paper mill may be prevented or reduced by treating the wastewater or process water (e.g., white water) of the pulp and paper mill with a carbohydrate oxidase.

In another preferred embodiment, the present invention relates to a method for preventing or reducing odors from paper recycling mills. In paper recycling mills, processes used to improve the brightness of the pulp, e.g., deinking, are often associated with odor formation due to the presence of carbohydrate material in water. Accordingly, the addition of a carbohydrate oxidase, e.g., in the deinking step, preferably with the use of deinking enzymes, may be used to reduce or prevent malodor.

The carbohydrate oxidase treatment of the present invention can also have the additional benefit of decreasing biochemical oxygen demand (BOD) and/or chemical oxygen demand (COD). Although not limited to any one theory of operation, the carbohydrate oxidase utilizes oxygen to oxidize the carbohydrate materials to organic acids, and as a result, there is a decrease in the BOD and COD. BOD and COD, and improvements thereof, can be measured using standard techniques known in the art.

The present invention also relates to deodorizing compositions comprising a carbohydrate oxidase. The deodorizing composition may be in any suitable form, such as, for example, a liquid (e.g., aqueous) carrier or a solid carrier, such as, a tablet. In addition to the carrier material, other ingredients may also be included in the deodorizing composition, such as, surfactants, stabilizers and other deodorizing agents.

The present invention also relates to deodorizing compositions consisting essentially of a carbohydrate oxidase, i.e., lacking a phenolic compound used for a deodorizing effect. The present invention also relates to deodorizing compositions consisting of a carbohydrate oxidase.

The present invention also relates to the use of organic acids, such as, for example, gluconic acid, lactobionic acid, and/or cellobionic acid as odor control agents. In this aspect of the invention, the, organic acids function directly as odor control agents, with or without the carbohydrate oxidase treatment. The organic acids may accordingly be added to compositions or processes in an amount effect to control (reduce or prevent) odor.

EXAMPLES

Example 1

Pulp from old corrugated cardboard (OCC) was treated with a mixture of cellulase (Celluclast 1.5 L, Novozymes A/S), amylase (Aquazyme 240 L, Novozymes A/S), and glucoamylase (Spirizyme Plus Novozymes A/S) at 5% consistency, 45° C. for 3 hrs. Enzyme dosage for each of the enzyme was 2 kg/ton of pulp. The pulp was filtered through a Whatman filter paper (No. 4). The filtrates were then treated with a carbohydrate oxidase (*Microdochium nivale* carbohydrate oxidase, Novozymes A/S) at a dosage of 20 mg protein/L, 40° C. for 1 hr. The level of hydrogen peroxide produced was determined by Quntofix® peroxide test sticks (commercially available from MACHEREY-NAGEL). All of the beakers containing the filtrates were placed into a water bath for incubation at 40° C. Some of the beakers were left open in the water bath to simulate the aerobic conditions, and others were closed to simulate the anaerobic conditions. After several days of incubation, a panel of 5 people smelled the water samples (filtrates) and gave them a rating on a level from 1 to 5, with 5 being the worst.

TABLE 1

| Treatment | Condition | Time, days | $H_2O_2$, mg/L | Odor Level |
|---|---|---|---|---|
| Control | Open Beaker - aerobic | 3 | 0 | 4 |
| Carbohydrate oxidase | Open Beaker - aerobic | 3 | 20 | 1 |
| Control | Capped Beaker - Anaerobic | 3 | 0 | 4 |
| Carbohydrate oxidase | Capped Beaker - Anaerobic | 3 | 20 | 1 |

The results show that carbohydrate oxidase treatment of the OCC waste water significantly reduced the formation of odor under both aerobic and anaerobic conditions.

Example 2

Pulps from mixed office waste (MOW) were treated as described in Example 1. The results are shown in Table 2.

TABLE 2

| Treatment | Condition | Time, days | $H_2O_2$, mg/L | Odor Level |
|---|---|---|---|---|
| Control | Open Beaker - aerobic | 3 | 0 | 5 |
| Carbohydrate oxidase | Open Beaker - aerobic | 3 | 10 | 3 |
| Control | Capped Beaker - Anaerobic | 3 | 0 | 5 |
| Carbohydrate oxidase | Capped Beaker - Anaerobic | 3 | 10 | 2 |

The results in Table 2 indicated that carbohydrate oxidase treatment can effectively prevent the odor formation from MOW waste water.

Example 3

Figure 2:
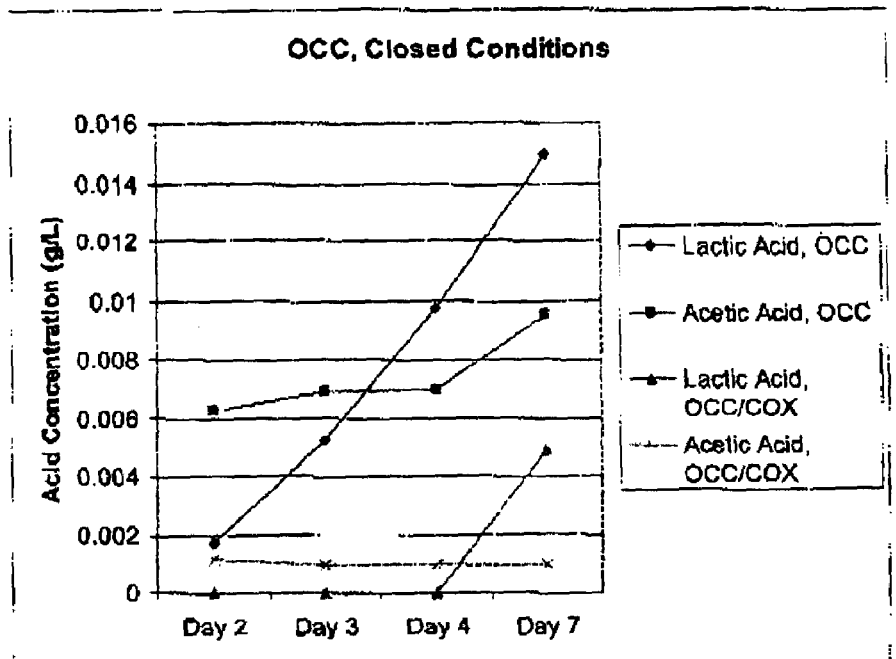
FIG. 2 is a graph generated from HPLC data for lactic acid and acetic acid concentration (g/L) in OCC filtrate, under closed atmospheric conditions.
Figure 3:
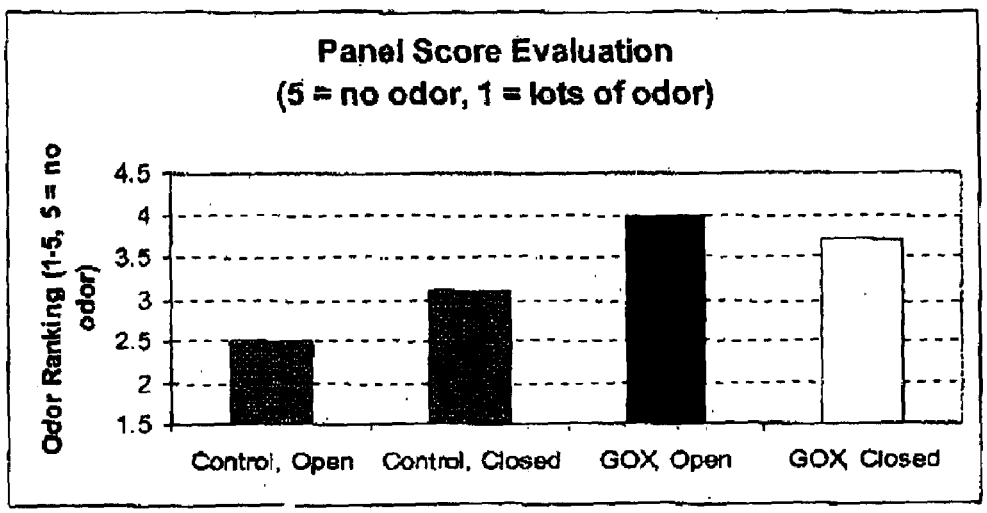
FIG. 3 is a table showing that the glucose oxidase was able to reduce the odor of the OCC furnish, and there is sufficient substrate from the microbial degradation of OCC furnish for odor reduction.

About 1 mL of filtrate was taken from the beakers in Example 1 at Day 2, 3, 4 and 7. The samples were then analyzed by HPLC. The formation of lactic acid and acetic acid with time is shown in FIGS. 1 and 2.

As shown in these figures, the carbohydrate oxidase treatment greatly reduced the formation of lactic acid and acetic acid under both aerobic and anaerobic conditions.

Example 4

250 mL of (1) 10 mM gluconic acid; (2) 10 mM glucose; and (3) 5 mM glucose/5 mM gluconic acid mixture were placed in beakers 1, 2 and 3, respectively. Another 250 mL of (4) 10 mM glucose was put it in beaker 4. 20 mg protein/L of carbohydrate oxidase (*Microdochium nivale* carbohydrate oxidase, Novozymes A/S) was added to beaker 4 and it was kept at a 40° C. for 1 hr. 0.5 mL of odorous 3-day filtrate from the aerobic control in Example 2 was added to all of the beakers. The beaker were capped and placed in a 40° C. water bath for 7 days. At the end of the incubation, a panel smelled the samples as described in Example 1.

TABLE 3

| Beaker No. | Samples | Odor Level |
|---|---|---|
| 1 | 10 mM Gluconic Acid | 1 |
| 2 | 10 mM Glucose | 5 |
| 3 | 5 mM Gluconic Acid/ 5 mM Glucose | 1 |
| 4 | 10 mM Glucose/ COX | 2 |

It is evident that gluconic acid, unlike glucose, will not lead to odorous smell. Even with a blend of gluconic acid and glucose (1:1 ratio), gluconic acid effectively reduced the formation of odor. When glucose was treated with carbohydrate oxidase, its tendency to produce odor was also substantially reduced.

Example 5

In this study, the OCC furnish was not treated with a hydrolase (amylase, glucoamylase, or cellulase) prior to the addition of the glucose oxidase in order to determine if there was sufficient substrate for the glucose oxidase from the microbial degradation of the OCC furnish.

An OCC sample (2 L of 5% consistency slurry for furnish (50 g/L)) was disintegrated for 10 minutes and the sample was aliquoted (500 ml) into large LOM beakers. The pulp was filtered from the liquor and discarded. Glucose oxidase was added to the appropriate beakers (equivalent to 2 kg/ton) at room temperature. Beakers were left open to the air at room temperature for three hours. An open and sealed control and enzyme sample were labeled and placed into a 40° C. water bath for 7 days. After the 7 days, a panel evaluation was done and the results are in FIG. 1. The control and enzyme treated sample were compared to each other for both the open and closed vessels and the glucose oxidase treated samples were selected as having less odor.

The invention claimed is:

1. A method for controlling malodor in a pulp and paper mill, comprising contacting the process water or waste water used in a pulp and paper mill with a deodorizing composition consisting essentially of a carbohydrate oxidase.

2. The method of claim 1, wherein the process water or waste water used in a pulp and paper mill comprises a carbohydrate material and a malodor generating agent.

3. The method of claim 2, wherein the malodor generating agent is a microorganism.

4. The method of claim 1, wherein said contacting results in a reduction in the formation of volatile short chain fatty acids.

5. The method of claim 1, wherein said carbohydrate oxidase is a hexose oxidase.

6. The method of claim 1, wherein said carbohydrate oxidase is a glucose oxidase.

7. A method for controlling malodor in a pulp and paper mill, comprising contacting the process water or waste water used in a pulp and paper mill with a deodorizing composition consisting of a carbohydrate oxidase.

8. The method of claim 7, wherein the process water or waste water used in a pulp and paper mill comprises a carbohydrate material and a malodor generating agent.

9. The method of claim 8, wherein the malodor generating agent is a microorganism.

10. The method of claim 7, wherein said contacting results in a reduction in the formation of volatile short chain fatty acids.

11. The method of claim 7, wherein said carbohydrate oxidase is a hexose oxidase.

12. The method of claim 7, wherein said carbohydrate oxidase is a glucose oxidase.

* * * * *